US011317576B2

(12) United States Patent
van den Bosch et al.

(10) Patent No.: US 11,317,576 B2
(45) Date of Patent: May 3, 2022

(54) *XANTHOMONAS* RESISTANT *BRASSICA OLERACEA* PLANTS

(71) Applicant: SEMINIS VEGETABLE SEEDS, INC., St. Louis, MO (US)

(72) Inventors: Franciscus van den Bosch, Kesteren (NL); Gerard N. Koorevaar, Ede (NL); Carl E. Mero, Arroyo Grande, CA (US)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 0 days.

(21) Appl. No.: 15/721,700

(22) Filed: Sep. 29, 2017

(65) Prior Publication Data
US 2018/0092318 A1 Apr. 5, 2018

Related U.S. Application Data

(60) Provisional application No. 62/402,781, filed on Sep. 30, 2016.

(51) Int. Cl.
*A01H 6/20* (2018.01)
*A01H 5/12* (2018.01)
*A01H 1/00* (2006.01)
*A01H 1/04* (2006.01)
*A01H 1/02* (2006.01)

(52) U.S. Cl.
CPC .............. *A01H 6/203* (2018.05); *A01H 1/02* (2013.01); *A01H 1/04* (2013.01); *A01H 1/045* (2021.01); *A01H 1/125* (2021.01); *A01H 5/12* (2013.01)

(58) Field of Classification Search
None
See application file for complete search history.

(56) References Cited

U.S. PATENT DOCUMENTS

| 6,207,367 B1 | 3/2001 | Helentjaris et al. |
| 9,000,258 B2 | 4/2015 | Ligthart et al. |

FOREIGN PATENT DOCUMENTS

WO    WO 2010/089374    8/2010

OTHER PUBLICATIONS

*Brassica oleracea*; Wikipedia; downloaded on Mar. 15, 2019; pp. 1-7 (Year: 2019).*
Tonu et al. Comparison of positions of QTLs conferring resistance to Xanthomonas campestris pv. campestris in *Brassica oleracea*. (2013) American Journal of Plant Sciences; vol. 4; pp. 11-20 (Year: 2013).*
Afrin et al. Identification of NBS-encoding genes linked to black rot resistance in cabbage (*Brassica oleracea* var. *capitata*. (2018) Molecular Biology Reports; vol. 45; pp. 773-785 (Year: 2018).*
Lee et al. Genome-wide SNP identification and QTL mapping for black rot resistance in cabbage. (2015) BMC Plant Biology; vol. 15; pp. 1-11 (Year: 2015).*
Vicente et al. Inheritance of race-specific resistance to Xanthomoas campestris pv. campestris in *Brassica* genomes. (2002) Phytopathology vol. 92; pp. 1134-1141). (Year: 2002).*
Camargo et al. Mapping of quantitative trait loci controlling resistance of *Brassica oleracea* to Xanthomonas campestris p.v. campestris in the field and greenhouse. (1995) Phytophathology; vol. 85; pp. 1296-1300 (Year: 1995).*
Vicente et al. Inheritance of race-specific resistance to Xanthomonas campestris pv. campestris in *Brassica* genomes. (2002) Phytopathology; vol. 92; pp. 1134-1141 (Year: 2002).*
Fernandes et al. Unleashing meiotic crossovers in hybrid plants. ((2018) PNAS; vol. 115; pp. 2431-2436 (Year: 2018).*
Cea et al. *Brassica oleracea* genome assembly, contig: Boleracea_scaffold_1, whole genome shotgun sequence. (2018) GenBank Accession OWNI02000001; p. 1 of 1 (Year: 2018).*
Tonu et al., "Comparison of Positions of QTLs Conferring Resistance to Xanthomonas campestris pv. campestris in *Brassica oleracea*," American Journal of Plant Sciences 4:11-20, 2013.
Mau et al., "Construction of a Linkage Map and QTL analysis for Black Rot Resistance in *Brassica oleracea* L.," International Journal of Natural Sciences 1(1):1-6, 2011.
Ignatov et al., "Vascular stem resistance to black rot in *Brassica oleracea*," Canadian Journal of Botany 77:442-446, 1999.
Figure 1 from Third-Party Opposition regarding Japanese Application No. 2017-190862, filed on Oct. 3, 2018 and Oct. 31, 2018.
Third-Party Opposition regarding Japanese Application No. 2017-190862, filed on Oct. 3, 2018.
Third-Party Opposition regarding Japanese Application No. 2017-190862, filed on Oct. 31, 2018.
Carmargo, et al., "Location of the Self-Incompatibility Locus in an RFLP and RAPD Map of *Brassica oleracea*," *The Journal of Heredity* 88:57-60, 1997.
Fargier et al., "Pathogenicity assays restrict the species *Xanthomonas campestris* into three pathovars and reveal nine races within *X. campestris* pv. *Campestris*," *Plant Pathology* 56:805-818, 2007.
Griffiths, "Introgression and characterization of black rot resistance derived from *Brassica carinata* in cole crops," New York State Vegetable Projects Relating to IPM #128:1-4. 2001.
Griffiths, "Breeding cabbage for resistance to black rot (*Xanthomonas campestris*)," New York State Vegetable Projects Relating to IPM #130: 6-11. 2003.

(Continued)

Primary Examiner — Cathy Kingdon Worley
(74) Attorney, Agent, or Firm — Dentons US LLP; Alissa Eagle

(57) ABSTRACT

The present disclosure provides *Brassica oleracea* plants exhibiting broad spectrum resistance to *Xanthomonas campestris* pv. *campestris*. Such plants may comprise novel introgressed genomic regions associated with disease resistance from *Brassica oleracea* var. *capitata*. In certain aspects, compositions, including novel polymorphic markers and methods for producing, breeding, identifying, and selecting plants or germplasm with a disease resistance phenotype are provided.

20 Claims, 3 Drawing Sheets

Specification includes a Sequence Listing.

(56) References Cited

OTHER PUBLICATIONS

Griffiths et al., "Evaluation of Black Rot Resistance in Cabbage Germplasm Derived from Intraspecific and Interspecific Crosses," *HortScience* 38(5):677, 2003.
Griffiths et al., "Response of *Brassica oleracea* var. *capitata* to Wound and Spray Inoculations with *Xanthomonas campestris* pv. *Campestris*," *HortScience* 40(1):1-3, 2005.
Griffiths et al., "Identification of Crucifer Accessions from the NC-7 and NE-9 Plant Introduction Collections That Are Resistant to Black Rot (*Xanthomonas campestris* pv. *campestris*) Races 1 and 4," *HortScience* 44(2):284-288, 2009.
Jensen et al., "Field evaluation for resistance to the black rot pathogen *Xanthomonas campestris* pv. *campestris* in cabbage (*Brassica oleracea*)," *European Journal of Plant Pathology* 113:297-308, 2005.
Jensen, et al., "Occurrence and diversity of *Xanthomonas campestris* pv. *campestris* in Vegetable *Brassica* fields in Nepal," *Plant Disease* 94:298-305, 2010.
Kamoun, et al., "Incompatible interaction between crucifers and *Xanthomonas campestris* involves a vascular hypersensitive response, role of the hrpX locus," *Molecular Plant-Microbe Interactions* 5: 22-33, 1992.
Saha et al., "Molecular mapping of black rot resistance locus Xca1bo on chromosome 3 in Indian cauliflower (*Brassica oleracea* var. *botrytis* L.)," *Plant Breeding* 133:268-274, 2014.
Soengas et al., "Identification of quantitative trait loci for resistance to *Xanthomonas campestris* pv. *campestris* in *Brassica rapa*," *Theor. Appl. Genet.* 114:637-645, 2007.
Tonguc et al., "Identification of Molecular Markers Linked to Black Rot Resistance in Cole Crops," *HortScience* 36(3):562, 2001.
Tonguc et al., "Segregation distortion of *Brassica carinata* derived black rot resistance in *Brassica oleracea*," *Eyphytica* 134:269-276, 2003.

Tonguc et al., "Evaluation of *Brassica carinata* Accessions for Resistance to Black Rot (*Xanthomonas campestris* pv. *Campestris*)," *HortScience* 39(5):952-954, 2004.
Tonu, "Genetic Analysis of Resistance to *Xanthomonas campestris* pv. *campestris* in *Brassica oleracea*," Doctoral Program in Life and Food Science. Graduate School of Science and Technology. Niigata University. 2013.
Vicente et al., "Resistance to *Xanthomonas campestris* pv. *Campestris* in *Brassica* spp.," 3rd ISHS International Symposium on Brassicas. 2000.
Vicente, J.G., et al., "Identification and origin of *Xanthomonas campestris* pv. *campestris* races and related pathovars," *Phytopathology* 91: 492-499, 2001.
Vicente et al., "Inheritance of Race-Specific Resistance to *Xanthomonas campestris* pv. *campestris* in *Brassica* Genomes," *Phytopathology* 92(10):1134-1141, 2002.
European Extended Search Report regarding European Application No. 17194031, dated Dec. 1, 2017.
Camargo et al., "Mapping of Quantitative Trait Loci Controlling Resistance of *Brassica oleracea* to *Xanthomonas campestris* p.v. *campestris* in the Field and Greenhouse," *Phytopathology* 85:1296-1300, 1995.
Kifuji et al., "QTL analysis of black rot resistance in cabbage using newly developed EST-SNP markers," *Euphytica* 190:289-295, 2012.
Lema et al., "Screening for resistance to black rot in *Brassica oleracea* crops," *Plant Breeding* 131:607-613, 2012.
Taylor et al., "Sources and Origin of Resistance to *Xanthomonas campestris* pv. *Campestris* in *Brassica* Genomes," *Phytopathology* 92:105-111, 2002.
Tonguc et al., "Development of black rot resistant interspecific hybrids between *Brassica oleracea* L. cultivars and *Brassica* accession A 19182, using embryo rescue," *Euphytica* 136:313-318, 2004.

* cited by examiner

SEQUENCE LISTING

<160> NUMBER OF SEQ ID NOS: 28

<210> SEQ ID NO 1
<211> LENGTH: 21
<212> TYPE: DNA
<213> ORGANISM: Artificial sequence
<220> FEATURE:
<223> OTHER INFORMATION: Probe

<400> SEQUENCE: 1
cattgactct tgtcttataa g                                          21

<210> SEQ ID NO 2
<211> LENGTH: 19
<212> TYPE: DNA
<213> ORGANISM: Artificial sequence
<220> FEATURE:
<223> OTHER INFORMATION: Probe

<400> SEQUENCE: 2
ttgactcttg tcttctaag                                                    19

<210> SEQ ID NO 3
<211> LENGTH: 25
<212> TYPE: DNA
<213> ORGANISM: Artificial sequence
<220> FEATURE:
<223> OTHER INFORMATION: Primer

<400> SEQUENCE: 3
atagacctaa ggtaacttga aacat                                             25

<210> SEQ ID NO 4
<211> LENGTH: 25
<212> TYPE: DNA
<213> ORGANISM: Artificial sequence
<220> FEATURE:
<223> OTHER INFORMATION: Primer

<400> SEQUENCE: 4
ccgggaacat agcaacaagt tagtt                                             25

<210> SEQ ID NO 5
<211> LENGTH: 121
<212> TYPE: DNA
<213> ORGANISM: Brassica oleracea
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 5
tttncatgct tctaccccna tagacctaag gtaacttgaa acatcattga ctcttgtctt        60
mtaagaggac actaactaac ttgttgctat gttcccggtg atgcagaaat ccgaggaagg       120
g                                                                      121

<210> SEQ ID NO 6
<211> LENGTH: 23
<212> TYPE: DNA
<213> ORGANISM: Artificial sequence
<220> FEATURE:
<223> OTHER INFORMATION: Probe

<400> SEQUENCE: 6
aaatctagaa actggataca gat                                               23

<210> SEQ ID NO 7
<211> LENGTH: 20
<212> TYPE: DNA
<213> ORGANISM: Artificial sequence
<220> FEATURE:
<223> OTHER INFORMATION: Probe

<400> SEQUENCE: 7
tctagaaact gggtacagat                                                    20

<210> SEQ ID NO 8
<211> LENGTH: 27
<212> TYPE: DNA
<213> ORGANISM: Artificial sequence
<220> FEATURE:
<223> OTHER INFORMATION: Primer

<400> SEQUENCE: 8
gtaaccgttt gtttaccttt ggattct                                            27

<210> SEQ ID NO 9
<211> LENGTH: 26
<212> TYPE: DNA
<213> ORGANISM: Artificial sequence
<220> FEATURE:
<223> OTHER INFORMATION: Primer

<400> SEQUENCE: 9
ccagagaatg caaatcagta gacgat                                             26

<210> SEQ ID NO 10
<211> LENGTH: 121
<212> TYPE: DNA
<213> ORGANISM: Brassica oleracea
<220> FEATURE:
<221> NAME/KEY: misc_feature
<222> LOCATION: (12)..(12)
<223> OTHER INFORMATION: n is a, c, g, or t

<400> SEQUENCE: 10
ggtctacaaa angtaaccgt ttgtttacct ttggattctt aattatactt ggtatctgta        60
yccagtttct agatttcctc ttggaatcgt ctactgattt gcattctctg gacatttta       120 g                                                                       121

<210> SEQ ID NO 11
<211> LENGTH: 121
<212> TYPE: DNA
<213> ORGANISM: Brassica oleracea

<400> SEQUENCE: 11
atggccttac ctgaagccag gagttcgaga cagggctaca ggagcggcag tgttggaagc        60
ragagaagca gtttctctca aggacgacaa acatttcagc gggccctatc tatgtctctc      120
t                                                                       121

<210> SEQ ID NO 12
<211> LENGTH: 121
<212> TYPE: DNA
<213> ORGANISM: Brassica oleracea

<400> SEQUENCE: 12
ctcggctgct ttaaaagcct tttcatgagc agaaacagtc ttctcctgct tggtttcttg        60
yttcttcttc atttcatacc agcgcctggc attaccgtgc gcagaaagtg ataggtcaac      120
c                                                                       121

<210> SEQ ID NO 13
<211> LENGTH: 18
<212> TYPE: DNA
<213> ORGANISM: Artificial sequence

```
<220> FEATURE:
<223> OTHER INFORMATION: Probe

<400> SEQUENCE: 13
agtaacctat caacttcg                                                    18

<210> SEQ ID NO 14
<211> LENGTH: 19
<212> TYPE: DNA
<213> ORGANISM: Artificial sequence
<220> FEATURE:
<223> OTHER INFORMATION: Probe

<400> SEQUENCE: 14
cagtaaccta tctacttcg                                                   19

<210> SEQ ID NO 15
<211> LENGTH: 25
<212> TYPE: DNA
<213> ORGANISM: Artificial sequence
<220> FEATURE:
<223> OTHER INFORMATION: Primer

<400> SEQUENCE: 15
tgggccagag attacaagat atcct                                            25

<210> SEQ ID NO 16
<211> LENGTH: 25
<212> TYPE: DNA
<213> ORGANISM: Artificial sequence
<220> FEATURE:
<223> OTHER INFORMATION: Primer

<400> SEQUENCE: 16
tgtctgcaga tgcaacttac ttcat                                            25

<210> SEQ ID NO 17
<211> LENGTH: 84
<212> TYPE: DNA
<213> ORGANISM: Brassica oleracea

<400> SEQUENCE: 17
aggccattga acaggtgggc cagagattac aagatatcct ccagggcgca gtaacctatc      60
wacttcgatg aagtaagttg catc                                             84

<210> SEQ ID NO 18
<211> LENGTH: 18
<212> TYPE: DNA
<213> ORGANISM: Artificial sequence
<220> FEATURE:
<223> OTHER INFORMATION: Probe

<400> SEQUENCE: 18
acagaacgag gttttgat                                                    18

<210> SEQ ID NO 19
<211> LENGTH: 16
<212> TYPE: DNA
<213> ORGANISM: Artificial sequence
<220> FEATURE:
<223> OTHER INFORMATION: Probe

<400> SEQUENCE: 19
agaacgaggc tttgat                                                      16
```

```
<210> SEQ ID NO 20
<211> LENGTH: 23
<212> TYPE: DNA
<213> ORGANISM: Artificial sequence
<220> FEATURE:
<223> OTHER INFORMATION: Primer

<400> SEQUENCE: 20
gcaaggtctt tgaacaggac atg                                              23

<210> SEQ ID NO 21
<211> LENGTH: 33
<212> TYPE: DNA
<213> ORGANISM: Artificial sequence
<220> FEATURE:
<223> OTHER INFORMATION: Primer

<400> SEQUENCE: 21
tgatgacttt aggttcagat ataactcctt agt                                   33

<210> SEQ ID NO 22
<211> LENGTH: 121
<212> TYPE: DNA
<213> ORGANISM: Brassica oleracea

<400> SEQUENCE: 22
atcagaatgc atgcaaggtc tttgaacagg acatgggggtt tctatcgtca cagaacgagg     60
ytttgatgaa ggagaaagta ccaactaagg agttatatct gaacctaaag tcatcagaca    120
c                                                                    121

<210> SEQ ID NO 23
<211> LENGTH: 19
<212> TYPE: DNA
<213> ORGANISM: Artificial sequence
<220> FEATURE:
<223> OTHER INFORMATION: Probe

<400> SEQUENCE: 23
caacttgttc acttcaccc                                                   19

<210> SEQ ID NO 24
<211> LENGTH: 18
<212> TYPE: DNA
<213> ORGANISM: Artificial sequence
<220> FEATURE:
<223> OTHER INFORMATION: Probe

<400> SEQUENCE: 24
aacttgttca cctcaccc                                                    18

<210> SEQ ID NO 25
<211> LENGTH: 22
<212> TYPE: DNA
<213> ORGANISM: Artificial sequence
<220> FEATURE:
<223> OTHER INFORMATION: Primer

<400> SEQUENCE: 25
tggctgcttc tggtactgtt tc                                               22

<210> SEQ ID NO 26
<211> LENGTH: 25
<212> TYPE: DNA
<213> ORGANISM: Artificial sequence
```

```
<220> FEATURE:
<223> OTHER INFORMATION: Primer

<400> SEQUENCE: 26
ctctctgtta tcaccttggt gttca                                          25

<210> SEQ ID NO 27
<211> LENGTH: 121
<212> TYPE: DNA
<213> ORGANISM: Brassica oleracea
<220> FEATURE:
<221> NAME/KEY: misc_feature
<222> LOCATION: (40)..(40)
<223> OTHER INFORMATION: n is a, c, g, or t

<400> SEQUENCE: 27
tatgaaatct caagtcatgg ctgcttctgg tactgtttcn ttgcttcagt tgcagggtga      60
rgtgaacaag ttgaatgaac accaaggtga taacagagag gagcatattc agaaagccat     120
t                                                                    121

<210> SEQ ID NO 28
<211> LENGTH: 232
<212> TYPE: DNA
<213> ORGANISM: Brassica oleracea

<400> SEQUENCE: 28
gtttccagcg gttcaattag gttctcctat cgagccacag acgatagagc agcgctacat      60
cgaagccatc aacggcattc ttcgcaagag cgctccaatm aaaacacggc cttctttcac     120
cctctctgct tcctcctctc ccaaatctga atcgtcacca gatgggtacg gtaacggtaa     180
cgagcagcct gagatgggta gctaccagtt gagccggctt tacccgatgc at            232
```

XANTHOMONAS RESISTANT BRASSICA OLERACEA PLANTS

CROSS-REFERENCE TO RELATED APPLICATIONS

This application claims the priority of U.S. Provisional Appl. Ser. No. 62/402,781, filed Sep. 30, 2016, the entire disclosure of which is incorporated herein by reference.

FIELD OF THE INVENTION

The present invention relates to the field of agriculture and more specifically to methods and compositions for producing *Brassica oleracea* plants exhibiting improved resistance to *Xanthomonas campestris* pv. *campestris*.

INCORPORATION OF SEQUENCE LISTING

The sequence listing that is contained in the file named "SEMB024US_ST25.txt", which is 10 kilobytes as measured in Microsoft Windows operating system and was created on Sep. 29, 2017, is filed electronically herewith and incorporated herein by reference.

BACKGROUND OF THE INVENTION

Disease resistance is an important trait in agriculture, particularly for the production of food crops. Although disease resistance alleles have been identified in *Brassica*, efforts to introduce these alleles into cultivated lines are hindered by a lack of specific markers linked to the alleles, linkage drag that leads to unacceptable plant quality and a lack of broad spectrum resistance. The use of marker-assisted selection (MAS) in plant breeding methods has made it possible to select plants based on genetic markers linked to traits of interest. However, accurate markers for identifying or tracking desirable traits in plants are frequently unavailable even if a gene associated with the trait has been characterized. These difficulties are further complicated by factors such as polygenic or quantitative inheritance, epistasis and an often incomplete understanding of the genetic background underlying expression of a desired phenotype.

SUMMARY OF THE INVENTION

The present invention provides a cultivated variety of a *Brassica oleracea* plant comprising an introgression from *Brassica oleracea* var. *capitata* chromosome 3 that confers broad-spectrum resistance to *Xanthomonas campestris* pv. *campestris* relative to a plant lacking the introgression, and wherein the resistance is co-dominant and additive. In certain embodiments the introgression lacks an allele genetically linked thereto conferring retarded plant growth. In further embodiments the introgression comprises a chromosomal segment from *Brassica oleracea* var. *capitata* flanked by marker NH0265157 (SEQ ID NO:5) and marker NH0266951 (SEQ ID NO:12) in the plant. In other embodiments the introgression comprises a chromosomal segment from *Brassica oleracea* var. *capitata* at marker NH0265597 (SEQ ID NO:11) in the plant. In additional embodiments the introgression is about 2 cM or less in size. In yet other embodiments the plant is homozygous for the introgression. In additional embodiments a sample of seed comprising the introgression was deposited under ATCC Accession Number PTA-123409.

In certain aspects the broad-spectrum resistance comprises resistance to a plurality of *Xanthomonas campestris* pv. *campestris* pathovars. For one example, the broad-spectrum resistance comprises resistance to *Xanthomonas campestris* pv. *campestris* pathovars 1 and 4. For another example, the broad-spectrum resistance comprises resistance to *Xanthomonas campestris* pv. *campestris* pathovars 1, 4, 6 and 9. In other embodiments the plant is a broccoli, cauliflower, sprouting broccoli, Brussels sprouts, white cabbage, red cabbage, savoy cabbage, curly kale cabbage, turnip cabbage or Portuguese cabbage plant. In yet other embodiments the plant is not a white cabbage plant.

The present invention additionally provides a seed that produces a cultivated variety of a *Brassica oleracea* plant comprising an introgression from *Brassica oleracea* var. *capitata* chromosome 3 that confers broad-spectrum resistance to *Xanthomonas campestris* pv. *campestris* relative to a plant lacking the introgression, and wherein the resistance is co-dominant and additive. The present invention also provides a plant part from a cultivated variety of a *Brassica oleracea* plant comprising an introgression from *Brassica oleracea* var. *capitata* chromosome 3 that confers broad-spectrum resistance to *Xanthomonas campestris* pv. *campestris* relative to a plant lacking the introgression, and wherein the resistance is co-dominant and additive. In certain embodiments the plant part is a cell, a seed, a root, a stem, a leaf, a head, a flower, or pollen.

In addition the present invention provides an introgression fragment comprising a chromosomal segment from *Brassica oleracea* var. *capitata* flanked by marker NH0265157 (SEQ ID NO:5) and marker NH0266951 (SEQ ID NO:12), an introgression fragment comprising a chromosomal segment from *Brassica oleracea* var. *capitata* at marker NH0265597 (SEQ ID NO:11), and an introgression fragment comprising a chromosomal segment from *Brassica oleracea* var. *capitata* wherein the fragment confers broad-spectrum resistance to *Xanthomonas campestris* pv. *campestris* and lacks an allele genetically linked thereto conferring retarded plant growth.

The present invention also provides a broccoli or cauliflower plant comprising an introgression from *Brassica oleracea* var. *capitata* chromosome 3 that confers broad-spectrum resistance to *Xanthomonas campestris* pv. *campestris* relative to a plant lacking the introgression, and wherein the resistance is co-dominant and additive.

The present invention further provides a method for producing a cultivated variety of a *Brassica oleracea* plant with improved resistance to *Xanthomonas campestris* pv. *campestris*, comprising introgressing into the plant variety a chromosomal segment from *Brassica oleracea* var. *capitata* chromosome 3 that confers broad-spectrum resistance to *Xanthomonas campestris* pv. *campestris* relative to a plant lacking the introgression, and wherein the resistance is co-dominant and additive. In certain embodiments the introgressing comprises crossing a plant comprising the chromosomal segment with itself or with a second *Brassica oleracea* plant of a different genotype to produce one or more progeny plants, and selecting a progeny plant comprising the chromosomal segment. In particular embodiments selecting a progeny plant comprises detecting at least one allele flanked by marker NH0265157 (SEQ ID NO:5) and marker NH0266951 (SEQ ID NO:12). In other embodiments selecting a progeny plant comprises detecting at least one allele at marker NH0265597 (SEQ ID NO:11). In further embodiments the progeny plant is an F2-F6 progeny plant. In selected embodiments the crossing comprises backcrossing.

In additional embodiments the backcrossing comprises from 2-7 generations of backcrosses.

In certain embodiments the plant variety is a broccoli, cauliflower, sprouting broccoli, Brussels sprouts, white cabbage, red cabbage, savoy cabbage, curly kale cabbage, turnip cabbage or Portuguese cabbage plant variety. In other embodiments the resistance comprises resistance to a plurality of *Xanthomonas campestris* pv. *campestris* pathovars. In yet other embodiments the resistance comprises resistance to *Xanthomonas campestris* pv. *campestris* pathovars 1 and 4. In still other embodiments the resistance comprises resistance to *Xanthomonas campestris* pv. *campestris* pathovars 1, 4, 6 and 9. In additional embodiments a sample of seed comprising the chromosomal segment was deposited under ATCC Accession Number PTA-123409.

The present invention further provides a cultivated variety of a *Brassica oleracea* plant with improved resistance to *Xanthomonas campestris* pv. *campestris*, produced by introgressing into the plant variety a chromosomal segment from *Brassica oleracea* var. *capitata* chromosome 3 that confers broad-spectrum resistance to *Xanthomonas campestris* pv. *campestris* relative to a plant lacking the introgression, and wherein the resistance is co-dominant and additive. The present invention also provides a method of producing food or feed comprising obtaining a *Brassica oleracea* plant, or a part thereof, with improved resistance to *Xanthomonas campestris* pv. *campestris*, that comprises an introgressed chromosomal segment from *Brassica oleracea* var. *capitata* chromosome 3 that confers broad-spectrum resistance to *Xanthomonas campestris* pv. *campestris* relative to a plant lacking the introgression, wherein the resistance is co-dominant and additive, and producing the food or feed from the plant or part thereof.

DETAILED DESCRIPTION

Figure 1:
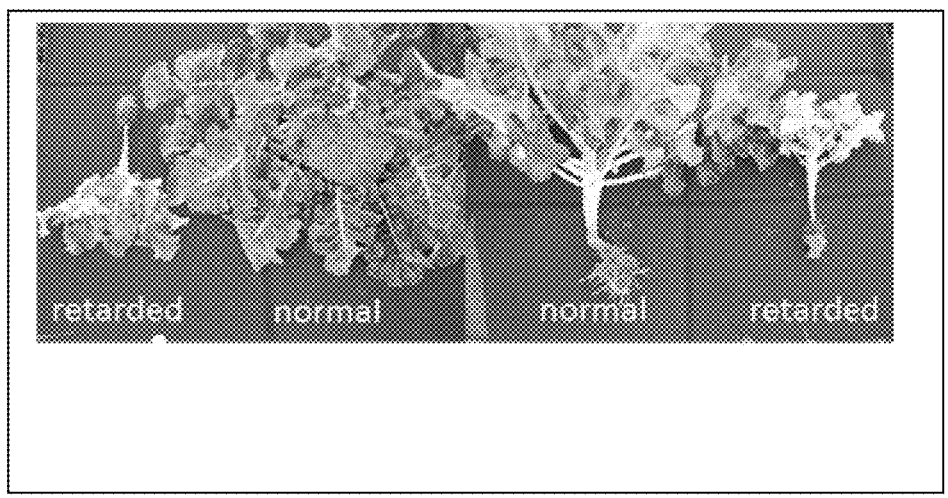
FIG. 1: This figure provides an example of plants with normal growth and retarded growth. Plants with retarded growth are smaller and often have purple leaves.

Black rot is a bacterial disease of crucifers caused by *Xanthomonas campestris* pv. *campestris* (Xcc). Xcc is transmitted by direct infection of developing seeds. Xcc is present across a wide geographical area and particularly affects cultivated varieties of *Brassica oleracea* by reducing yield and quality. Black rot or Xcc causes significant economic damage in cultivated varieties of *Brassica oleracea*, including, but not limited to, Brussels sprouts, cabbage, cauliflower, broccoli, and kale. Although there have been many previous efforts to develop resistant varieties and incorporate resistance genes in cultivated varieties of *Brassica oleracea*, none of these have been successfully used to obtain broad spectrum resistance in cultivated varieties of *B. oleracea*, and particularly to provide resistance in broccoli and cauliflower.

The classification of pathovars or races of *Xanthomonas campestris* pv. *campestris* has been undertaken by various groups with some variation in the classification and numbers of races or pathovars. At least 7 pathovars of Xcc have been identified Vicente, et al., *Phytopathology* 91:492-499, 2001; Fargier and Manceau, *Plant Pathology* 56:805-818, 2007; Jensen, et al., *Plant Disease* 94:298-305, 2010. These pathovars will often co-occur with one dominant pathovar. Races 1 and 4 are considered of major importance. It is important to identify a resistance allele, preferably a single gene, and for the allele to provide resistance to more than two races of Xcc. In addition, it is important to identify an allele that can be used to develop cultivated varieties of *Brassica oleracea* plants that have resistance against multiple races of Xcc ("broad spectrum resistance"). It is particularly important to identify an allele that can be used to develop cultivated varieties of broccoli and cauliflower that have resistance against multiple races of Xcc ("broad spectrum resistance").

The present invention represents a significant advance in that it provides a single resistance QTL that provides resistance to at least two pathovars of Xcc, and more particularly to at least pathovars 1 and 4. This QTL can be introgressed into elite lines of cultivated varieties of *Brassica oleracea*. These varieties can include, but are not limited to, cultivated varieties of broccoli, cauliflower, sprouting broccoli, Brussels sprouts, white cabbage, red cabbage, savoy cabbage, curly kale cabbage, turnip cabbage and Portuguese cabbage. In addition, the current invention provides a resistant locus without an associated allele that confers retarded growth relative to a plant that lacks the associated allele. Such retarded growth may include a slower rate of plant growth, as well as a reduced overall mature plant size.

Although a number of groups have attempted to identify sources for resistance to Xcc that can be used to provide resistance in cultivated varieties of *B. oleracea*, breeders have not been able to successfully transfer the resistance to commercially acceptable varieties for other *B. oleracea* types, or in obtaining varieties with resistance to multiple pathovars of Xcc. No source from *B. oleracea* has been identified that has resistance to at least races 1 and 4. Furthermore, a single co-dominant additive allele has not been identified. As such, the present invention provides a novel allele which provides broad spectrum resistance that can be incorporated into cultivated varieties of *B. oleracea*, and particularly into broccoli and cauliflower.

Multiple resistance loci have been identified in cabbage (*Brassica oleracea* var. *capitata*; Camargo, et al., *Genetics* 85:1296-1300, 1995 ("Carmargo, 1995"); Camargo, et al., *The Journal of Heredity* 88:57-60, 1997 ("Carmargo, 1997")). The QTLs reported by Camargo, 1995 were initially identified on separate linkage groups. However, subsequent analysis of these data using data from the published map of Camargo, 1997 revealed that these two QTL were linked (30 cM distance). Since the two loci are linked, breeders, in the process of selecting the most resistant plants, transfer not only the resistance loci from the donor cabbage plant into the recipient plant, but also the undesirable region in between, which leads to horticulturally and commercially unacceptable *Brassica oleracea* types. This region is not removed during selection from backcrosses. In addition, two recessive resistance loci have also been identified in cabbage (U.S. Pat. No. 9,000,258). However, both of these resistance alleles must be present to obtain an efficacious resistant phenotype.

Although *Brassica oleracea* hosts have been identified that are resistant to multiple Xcc isolates (Taylor, 2002), these resistances have been found to be limited to the less common races and none have provided resistance to both races 1 and 4. In other cases, the resistance was found to be partial and quantitative (Lema, et al., *Plant Breeding* 131: 607-613, 2012 ("Lema, 2012")). The race non-specific resistances depend on the combined action of various genes each of which has a small effect. These resistances are therefore hard to manage and transfer between cultivars. Most of the publications have concluded that the resistance follows a gene-for-gene model and that the resistance provided is race specific. Each different resistance gene was generally believed to provide resistance against one pathovar. Saha, et al. (*Plant Breeding* 133:268-274, 2014) identified a single dominant resistance QTL from a cauliflower source. However, this was shown to have resistance only to race 1.

The single resistance QTL of the present invention was identified on chromosome 3 (O3). The initial resistance allele identified was found to be tightly associated with a retarded growth plant type locus. However, the present invention also provides a smaller introgression fragment, which breaks the linkage. It was surprisingly found that a recombined chromosomal fragment could be generated that lacks the deleterious retarded growth plant type. The recombined introgression fragment was identified using marker assisted breeding techniques and the introgression fragment generated had a size of about 2 centiMorgans (cM). The mapping of this chromosomal segment found that the QTL for *Xanthomonas* resistance is located at marker NH0265597 (76.45 cM). Furthermore, the QTL is flanked by markers NH0265157 (74.98 cM) and NH0266951 (77.14 cM). This QTL results in resistance to several different Xcc pathovars, including pathovars 1 and 4, without the deleterious retarded growth plant type.

The resistance based on the recombined introgression is additive. Therefore, it is preferable for the QTL to be homozygous in hybrid plants, particularly for commercial hybrids. It is also generally preferable to use the smallest introgression fragment comprising the *Xanthomonas* resistance since the homozygous presence of other associated alleles can cause expression of deleterious recessive traits.

The recombined introgression provided by the present invention has been shown to provide resistance to a variety of different pathovars, including the currently prevalent pathovars 1, 4, 6 and 7, along with several unclassified isolates. The resistance QTL was tested against a group of 157 Xcc isolates from *Brassica oleracea* crops (broccoli, cauliflower, cabbage) that were identified from areas around the world. The isolates were classified using the improved differential plant series of Vicente, 2001, which is the current standard for the scientific community, and most of the isolates could be classified into pathovar groups 1, 4, 6 and 9. However, some of the isolates could not be classified. The differential set of Vicente consists of different *Brassica* plant species and enables pathovar differentiation based on compatible (susceptibility) and incompatible (resistance) interactions. This set can therefore be used to phenotypically confirm the broad-spectrum disease resistance conferred by the invention.

I. *Brassica oleracea* Plants

*Brassica* is a plant genus of the family of brassicaceae (formerly referred to as cruciferae). The members of this genus are also known as cabbage or mustard. The genus *Brassica* comprises a number of commercially and agriculturally important species. Of all those species *Brassica oleracea* is the most diverse containing at least ten different commercial cultivated varieties, including broccoli, cauliflower, sprouting broccoli, Brussels sprouts, white cabbage, red cabbage, savoy cabbage, curly kale cabbage, turnip cabbage and Portuguese cabbage. Breeding between these types is common and easily done because these types, while highly diverse phenotypically, are the same species, which means that a cross between the different types can be made without having to overcome any genetic species barrier. However, significant linkage drag can still occur for inter-cultivar crosses, especially when crossing between (genetically) distant cultivars (e.g., a cross between white cabbage and broccoli or cauliflower). Thus while the absence of a species barrier allows crosses to be made between all cultivars, it is likely that linkage drag will be associated with such a cross.

II. Genomic Regions, Alleles, and Polymorphisms Associated with Black Rot (Xcc) Resistance in *Brassica oleracea* Plants Black rot is a bacterial disease in *Brassica oleracea* caused by *Xanthomonas campestris* pv. *campestris* (Xcc). Although some sources of black rot resistance have been identified, this resistance has not been successfully transferred to cultivated varieties of *Brassica oleracea*, and in particular to broccoli and cauliflower. In addition, a single, co-dominant, additive QTL has not been previously identified.

It is therefore desirable to identify specific genomic regions conferring a desired black rot (Xcc) resistance. It is also desirable to provide resistance with a single gene and to provide a gene having more durable resistance. Such a region should not include alleles associated with deleterious traits. In addition, resistance associated with a single gene is less likely to be broken down during breeding, which results in more durable resistance. The introgression identified herein or any introgression with a reduced introgression size has not been achieved previously. Moreover, no effective markers which are closely linked to resistance have been described.

Using the genetic markers and assays of the invention, Applicants were surprisingly able to identify a novel Xcc resistance region from *Brassica oleracea* var. *capitata*, identified in a cross between the publicly known cabbage line C517 and an elite broccoli line (BRL51-99sc). The mapping of this introgression indicated that the QTL for Xcc resistance is located at marker NH0265597 (76.45 cM), and flanked by markers NH0265157 (74.98 cM) and NH0266951 (77.14 cM). One of skill in the art will understand that interval values may vary based on factors such as the reference map that is used, the sequencing coverage and the assembly software settings. However, such parameters and mapping protocols are known in the art and one of skill in the art can use the marker sequences provided herein to physically and genetically anchor the introgressions described herein to any given map using such methodology. The novel introgression of the present invention confers unique significantly improved agronomic properties over previously disclosed Xcc resistance introgressions.

III. Introgression of Genomic Regions Associated with Disease Resistance

Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The present invention provides novel markers for identifying and tracking introgression of one or more of the genomic regions from *Brassica oleracea* var. *capitata*, initially identified in a cross between cabbage line C517 (public source) and an elite broccoli line (BRL51-99sc), disclosed herein into cultivated *Brassica oleracea* lines. The invention further provides markers for identifying and tracking the novel introgressions disclosed herein during plant breeding, including markers NH0265597 (76.45 cM), NH0265157 (74.98 cM) and NH0266951 (77.14 cM).

Markers within or linked to any of the genomic intervals of the present invention can be used in a variety of breeding efforts that include introgression of genomic regions associated with disease resistance into a desired genetic background. For example, a marker within 20 cM, 15 cM, 10 cM, 5 cM, 2 cM, or 1 cM of a marker associated with disease resistance described herein can be used for marker-assisted introgression of genomic regions associated with a disease tolerant phenotype.

*Brassica oleracea* plants comprising one or more introgressed regions associated with a desired phenotype wherein at least 10%, 25%, 50%, 75%, 90%, or 99% of the remaining genomic sequences carry markers characteristic of the germplasm are also provided. *Brassica oleracea* plants comprising an introgressed region comprising regions closely linked to or adjacent to the genomic regions and markers provided herein and associated with an Xcc disease resistance phenotype are also provided.

IV. Development of Disease Resistant *Brassica oleracea* Varieties

For most breeding objectives, commercial breeders work within germplasm that is "cultivated type" or "elite." This germplasm is easier to breed because it generally performs well when evaluated for horticultural performance. Numerous elite *Brassica oleracea* crop cultivated varieties (cultivars) have been developed, including, but not limited to, broccoli, cauliflower, sprouting broccoli, Brussels sprouts, white cabbage, red cabbage, savoy cabbage, curly kale cabbage, turnip cabbage and Portuguese cabbage. However, the performance advantage a cultivated or elite germplasm provides can be offset by a lack of allelic diversity. Breeders generally accept this tradeoff because progress is faster when working with cultivated material than when breeding with genetically diverse sources.

The process of introgressing desirable resistance genes from non-cultivated lines into elite cultivated lines while avoiding problems with linkage drag or low heritability is a long and often arduous process. Success in deploying alleles derived from wild relatives therefore strongly depends on minimal or truncated introgressions that lack detrimental effects and reliable marker assays that replace phenotypic screens. Success is further defined by simplifying genetics for key attributes to allow focus on genetic gain for quantitative traits such as disease resistance. Moreover, the process of introgressing genomic regions from non-cultivated lines can be greatly facilitated by the availability of informative markers.

One of skill in the art would therefore understand that the alleles, polymorphisms, and markers provided by the invention allow the tracking and introduction of any of the genomic regions identified herein into any genetic background to which a *Brassica oleracea* species can be crossed. In addition, the genomic regions associated with disease resistance disclosed herein can be introgressed from one genotype to another and tracked phenotypically or genetically. Thus, Applicants' development markers for the selection of the disease resistance facilitates the development of *Brassica oleracea* plants having beneficial phenotypes. For example, plants and seeds can be genotyped using the markers of the present invention in order to develop varieties comprising desired disease resistance. Moreover, marker-assisted selection (MAS) allows identification of plants which are homozygous or heterozygous the desired introgression.

Meiotic recombination is essential for plant breeding because it enables the transfer of favorable alleles across genetic backgrounds, the removal of deleterious genomic fragments, and pyramiding traits that are genetically tightly linked. In the absence of accurate markers, limited recombination forces breeders to enlarge segregating populations for progeny screens. Moreover, phenotypic evaluation is time-consuming, resource-intensive and not reproducible in every environment, particularly for traits like disease resistance. The markers provided by the invention offer an effective alternative and therefore represent a significant advance in the art.

V. Molecular Assisted Breeding Techniques

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Vegetable breeders use molecular markers to interrogate a crop's genome and classify material based on genetic, rather than phenotypic, differences. Advanced marker technologies are based on genome sequences, the nucleotide order of distinct, polymorphic genotypes within a species. Such platforms enable selection for horticultural traits with markers linked to favorable alleles, in addition to the organization of germplasm using markers randomly distributed throughout the genome. In the past, a priori knowledge of the genome lacked for major vegetable crops that now have been sequenced. Scientists exploited sequence homology, rather than known polymorphisms, to develop marker platforms. Man-made DNA molecules are used to prime replication of genome fragments when hybridized pair-wise in the presence of a DNA polymerase enzyme. This synthesis, regulated by thermal cycling conditions that control hybridization and replication of DNA strands in the polymerase chain reaction (PCR) to amplify DNA fragments of a length dependent on the distance between each primer pair. These fragments are then detected as markers and commonly known examples include AFLP and RAPD. A third technique, RFLP does not include a DNA amplification step. Amplified fragment length polymorphism (AFLP) technology reduces the complexity of the genome. First, through digestive enzymes cleaving DNA strands in a sequence-specific manner. Fragments are then selected for their size and finally replicated using selective oligonucleotides, each homologous to a subset of genome fragments. As a result, AFLP technology consistently amplifies DNA fragments across genotypes, experiments and laboratories.

Polymorphisms comprising as little as a single nucleotide change can be assayed in a number of ways. For example, detection can be made by electrophoretic techniques including a single strand conformational polymorphism (Orita, et al., *Genomics* 8:271-278, 1989), denaturing gradient gel electrophoresis (Myers, EP 0273085), or cleavage fragment length polymorphisms (Life Technologies, Inc., Gathersberg, Md.), but the widespread availability of DNA sequencing often makes it easier to simply sequence amplified products directly. Once the polymorphic sequence difference is known, rapid assays can be designed for progeny testing, typically involving some version of PCR amplification of specific alleles (PASA; Sommer, et al., *Biotechniques* 12:82-87, 1992), or PCR amplification of multiple specific alleles (PAMSA; Dutton and Sommer, *Biotechniques* 11:700-702, 1991).

Polymorphic markers serve as useful tools for assaying plants for determining the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a *Brassica oleracea* plant a genotype associated with disease resistance, identify a *Brassica oleracea* plant with a genotype associated with disease resistance, and to select a *Brassica oleracea* plant with a genotype associated with disease resistance. In certain embodiments of methods of the invention, polymorphic nucleic acids can be used to produce a *Brassica oleracea* plant that comprises in its genome an introgressed locus associated with disease resistance. In certain embodiments of the invention, polymorphic nucleic acids can be used to breed progeny *Brassica oleracea* plants comprising a locus associated with disease resistance.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e., for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with disease resistance in *Brassica oleracea* plants.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al., *Cold Spring Harbor Symp. Quant. Biol.* 51:263-273, 1986; European Patent 50,424; European Patent 84,796; European Patent 258,017; European Patent 237,362; European Patent 201,184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entirety. However, the compositions and methods of the present invention can be used in conjunction with any polymorphism typing method to type polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz, et al., *Genome Res.* 13:513-523, 2003; Cui, et al., *Bioinformatics* 21:3852-3858, 2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996,476.

Other methods for detecting SNPs and Indels include single base extension (SBE) methods. Examples of SBE methods include, but are not limited, to those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays.

Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which *Brassica oleracea* plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "Quantitative Trait Locus (QTL)" is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, "elite line" or "cultivated line" means any line that has resulted from breeding and selection for superior agronomic performance. An "elite plant" refers to a plant belonging to an elite line. Numerous elite lines are available and known to those of skill in the art of *Brassica oleracea* breeding. An "elite population" is an assortment of elite individuals or lines that can be used to represent the state of the art in terms of agronomically superior genotypes of a given crop species, such as a *Brassica oleracea* line. Similarly, an "elite germplasm" or elite strain of germplasm is an agronomically superior germplasm. A cultivated variety of *Brassica oleracea* is not intended to encompass the C517 white cabbage source.

As used herein, the term "introgressed," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, marker assisted selection.

As used herein, the term "linked," when used in the context of nucleic acid markers and/or genomic regions, means that the markers and/or genomic regions are located on the same linkage group or chromosome such that they tend to segregate together at meiosis.

As used herein, "resistance locus" means a locus associated with resistance or tolerance to disease. For instance, a resistance locus according to the present invention may, in one embodiment, control resistance or susceptibility to black rot.

As used herein, "resistance allele" means the nucleic acid sequence associated with resistance or tolerance to disease.

As used herein "resistance" or "improved resistance" in a plant to disease conditions is an indication that the plant is less affected by disease conditions with respect to yield, survivability and/or other relevant agronomic measures, compared to a less resistant, more "susceptible" plant. Resistance is a relative term, indicating that a "resistant" plant survives and/or produces better yields in disease conditions compared to a different (less resistant) plant grown in similar disease conditions. As used in the art, disease "tolerance" is sometimes used interchangeably with disease "resistance." One of skill will appreciate that plant resistance to disease conditions varies widely, and can represent a spectrum of more-resistant or less-resistant phenotypes. However, by simple observation, one of skill can generally determine the relative resistance or susceptibility of different plants, plant lines or plant families under disease conditions, and furthermore, will also recognize the phenotypic gradations of "resistant."

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

VI. Deposit Information

A deposit was made of at least 2500 seeds of cauliflower strain C517xBRL51-99, which comprises an introgression from *Brassica oleracea* var. *capitata*, as described herein. The deposit was made with the American Type Culture Collection (ATCC), 10801 University Boulevard, Manassas, Va. 20110-2209 USA. The deposit is assigned ATCC Accession No. PTA-123409, and the date of deposit was Aug. 4, 2016. Access to the deposit will be available during the pendency of the application to persons entitled thereto upon request. The deposit will be maintained in the ATCC Depository, which is a public depository, for a period of 30 years, or 5 years after the most recent request, or for the enforceable life of the patent, whichever is longer, and will be replaced if nonviable during that period. Applicant does not waive any infringement of their rights granted under this patent or any other form of variety protection, including the Plant Variety Protection Act (7 U.S.C. 2321 et seq).

Example 1

Identification of Xcc Resistance Allele and Mapping

A Doubled Haploid (DH) population was constructed to identify resistance alleles. A cabbage breeding line (C517) was crossed with an elite broccoli line (BRL51-99sc) from *Seminis* Vegetable Seeds, Inc. to produce a hybrid. The hybrid was used to produce DH plants. These DH0 plants were selfed and the subsequent DH1 population were used to conduct a black rot test under greenhouse conditions. Briefly, the black rot test involves the following procedure: *Brassica* seedlings at the 5-6 true leaf stage are used as test material. The seedlings are grown under normal greenhouse conditions in a 12 cm pot with soil. A suspension of *Xanthamonas campestris campestris* at a concentration of $1 \times 10^6$ cells/mL is used to inoculate the seedlings. The seedlings are infected with the bacteria by injecting 0.2 mL of the Xcc suspension into the stem at two different points using a syringe. The response of the seedlings is recorded when controls are starting to show the expected reactions, which generally is around 14 days post infection. Symptoms are scored on a scale of 1-9 with 1 being no symptoms (resistant) and 9 being many necrotic spots and/or death of the plants (susceptible). Intermediate phenotypes are: 2: about two small spots visible on whole plant (total impression of plant is resistant); 3: very few chlorotic spots on the leaves (total impression of plant is resistant); 4: chlorotic spots on about 30% of leaf surface and whole plant (total impression of plant is IR); 5: chlorotic spots on about 40% of the leaf surface (total impression is IR), 6: chlorotic and necrotic spots on about 50% of leaves and whole plant (IR); 7: chlorotic and necrotic spots on about 60% of the leaf surface (susceptible); 8: necrotic spots on more than 70% of the leaf surface and whole plant (susceptible). Each experiment will include controls to compare against the tested seedlings. These controls may include the original parents of the mapping population.

Figure 2:
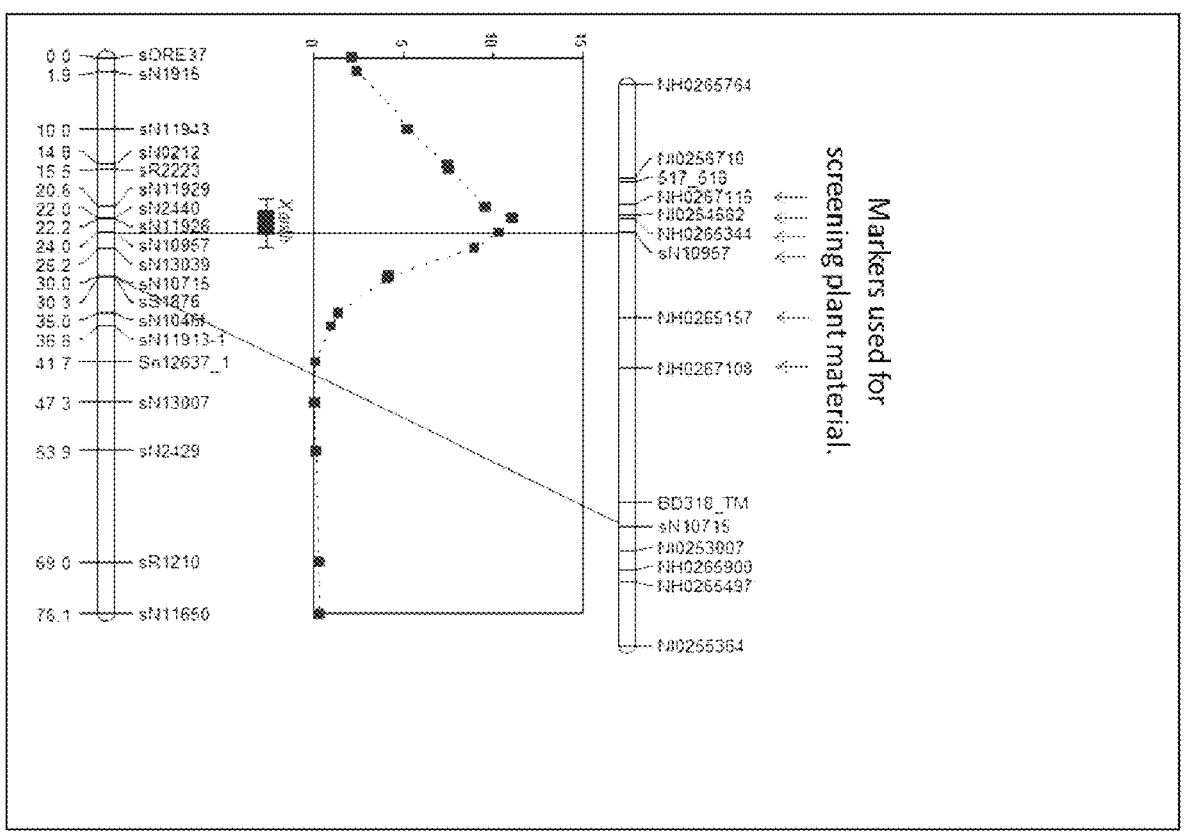
FIG. 2: The C517 QTL is identified on 2 cM scale, and markers are provided in the QTL region (5 cM). Markers used for screening the plant material are indicated with arrows.

A molecular marker map was constructed using SSR loci. Combining the map and the quantitative disease data resulted in the detection of one major QTL for black rot resistance at chromosome O3 (FIG. 2).

Example 2

Multiple Isolate Resistance

157 Xcc isolates were collected from *Brassica oleracea* crops (broccoli, cauliflower, cabbage) from all over the world. In this collection, isolates were classified using the improved differential plant series (Vicente, 2001), mostly as pathovar 1, 4, 6 and 9. Some isolates could not be classified into a pathovar group according to the Vicente, 2001 method. The distribution of pathovars across the world was not geographically linked, which corresponds to previous findings (Vicente, 2001; Taylor, 2002). All major pathovars were found to be present on every continent. This suggests that there is variation in Xcc for all growing areas worldwide. All isolates were then tested against the resistance QTL following the protocol described in Example 1. It was found that the resistance QTL provided resistance against all tested isolates (Table 1).

TABLE 1

Isolates collected from different countries were used to artificially infect C517. Results are shown as number of Susceptible (S), Intermediate Resistance (IR) and Resistant (R) reactions for C517. NP = non pathogenic.

| Country | Area | # of Xcc isolates | C517 (White cabbage) |
| --- | --- | --- | --- |
| India | North | 32 | S: 0; IR: 3; R: 29 |
| India | West | 22 (NP: 11) | S: 0; IR: 3; R: 8 |
| India | South | 46 | S: 0; IR: 0; R: 46 |
| India | East | 28 (NP: 8) | S: 0; IR: 0; R: 20 |
| China | | 7 | S: 0; IR: 4; R: 3 |
| France | | 5 | S: 0; IR: 0; R: 5 |
| Italy | | 3 | S: 0; IR: 0; R: 3 |
| Mexico | | 21 | S: 0; IR: 2; R: 19 |
| Poland | | 4 | S: 0; IR: 4; R: 0 |
| Spain | | 5 | S: 0; IR: 0; R: 5 |
| Turkey | | 2 | S: 0; IR: 1; R: 1 |
| total | | 157 | R-IR with all isolates |

Example 3

Removing Linkage Drag in Broccoli

Initial crosses between Xcc resistant breeding line (C517) and broccoli line (BRL51-99sc) resulted in linkage drag that was associated with the resistance locus. These plants showed retarded growth and/or small plant type (FIG. 1). The original DH1 population was further back-crossed with BRL51-99sc and subsequently selfed to generate more recombinants that could be used for fine-mapping of the Xcc resistance locus and removal of the linkage drag. Seeds from these families were sown in seedling trays in unheated greenhouses and grown for 6 weeks. Seedlings were planted in a randomized complete block design (2 replications and 20 plants per plot) on a trial field. Plants were evaluated after approximately three months. Plants segregated randomly within plots for head quality and leaf type. In the whole trial, there was segregation for retarded growth (see FIG. 1). Plants were scored for this trait with 1=retarded growth, 3=normal growth, 2=intermediate growth and 0=no observation.

The plants were then screened for six markers as indicated in FIG. 2 which are positioned around the QTL. Four (4) plants obtained from plots which were not segregating for retarded growth were sampled and all plants for plots segregating for retarded growth were sampled. The retarded growth trait is highly correlated with the resistance QTL from markers NH0267115 to NH0267108 and appears to be recessive (Table 2). Recombinants with a homozygous O3 introgression from NH0267115 to sN10957 and recurrent parent (HP99) for NH0265157 and NH0267108 do not show retarded growth.

TABLE 2

Observed genotypes for markers around the QTL for blackrot and the number of plants per plant scores for these genotypes. 1 = retarded growth, 3 = normal growth, 2 = intermediate growth and 0 = no observation

| | Genotypes | | | | | | Plant scores | | | |
|---|---|---|---|---|---|---|---|---|---|---|
| | NH0267115 | NI0254582 | NH0265344 | sN10957 | NH0265157 | NH0267108 | 1 | 2 | 3 | 0 |
| Genotype 1 | C517 | C517 | C517 | C517 | C517 | C517 | 779 | 376 | 32 | 3 |
| Genotype 2 | Het | Het | Het | Het | Het | Het | 4 | 8 | 106 | 10 |
| Genotype 3 | HP99 | HP99 | HP99 | HP99 | HP99 | HP99 | 1 | 13 | 125 | 5 |
| Genotype 4 | C517 | C517 | C517 | C517 | Het | Het | 9 | 3 | 25 | 4 |
| Genotype 5 | C517 | C517 | C517 | C517 | HP99 | HP99 | 1 | 1 | 12 | 1 |

Figure 3:
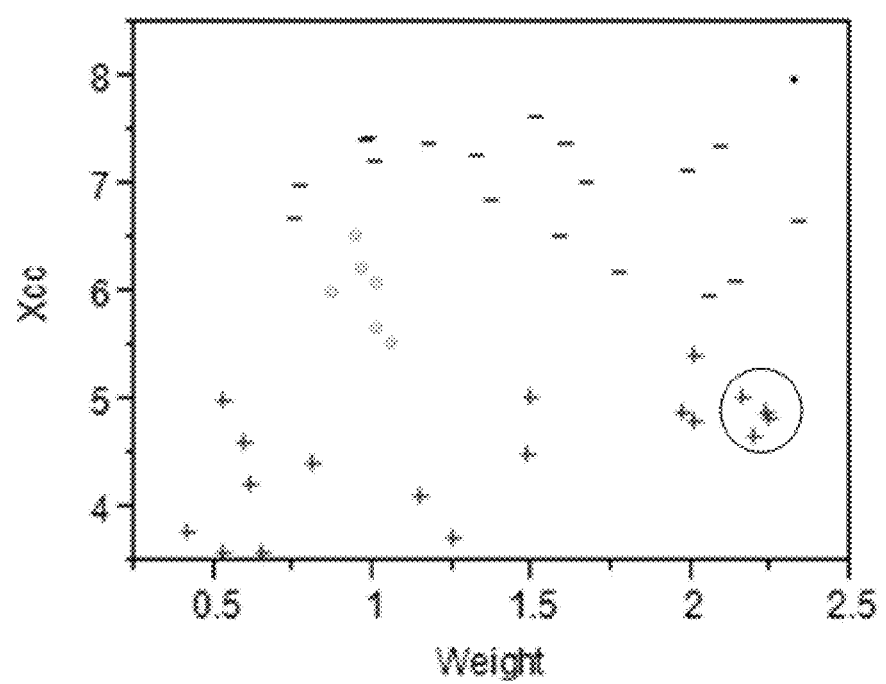
FIG. 3: This figure provides the correlation between total plant weight and resistance. The average total plant weight is provided on the X-axis and the average resistance to Xcc is provided on the Y-axis. Resistance to Xcc is measured on a scale from 1 (=resistant) to 9 (=susceptible) and total plant weight is measured in kilograms (kg). The most closely linked marker segregated in these lines: Plusses indicate homozygous resistance, minuses indicate homozygous susceptible and dots indicate heterozygote lines. The black dot in the upper right corner of the graph is the BRL51-99 line. The plants in the circle on the bottom right indicate the lines with a high level of resistance and without linkage drag on plant weight.

Based on QTL mapping (FIG. 2) and linkage drag results (Table 2), plants were selected based on recombination between sN10957 and NH0265157. Resistance is located left from sN10957 and drag is located right from sN10957. 24 recombinant plants and some checks were identified and brought into the greenhouse to produce seed for experiments. The plants generated from these seeds were tested for *Xanthomonas* resistance and plant weight in the field. In a correlation between plant weight and resistance level, the plants without linkage drag were selected (FIG. 3). All of these plants were found to have the smaller introgression from C517 on chromosome 3. The mapping of this introgression found that the QTL for *Xanthomonas* resistance is at most 2 cM in size and is located at marker NH0265597 (76.45 cM). Furthermore, the QTL is flanked by markers NH0265157 (74.98 cM) and NH0266951 (77.14 cM).

The sequences for the probes, primers and markers in Table 2 are shown in Table 3.

TABLE 3

| Marker | Probe Sequence 1 | Probe Sequence 2 | For. Primer Sequence | Rev. Primer Sequence | Sequence |
|---|---|---|---|---|---|
| NH0265157 | SEQ ID NO: 1 | SEQ ID NO: 2 | SEQ ID NO: 3 | SEQ ID NO: 4 | SEQ ID NO: 5 |
| NH0265344 | SEQ ID NO: 6 | SEQ ID NO: 7 | SEQ ID NO: 8 | SEQ ID NO: 9 | SEQ ID NO: 10 |
| NH0265597 | | | | | SEQ ID NO: 11 |
| NH0266951 | | | | | SEQ ID NO: 12 |
| NH0267108 | SEQ ID NO: 13 | SEQ ID NO: 14 | SEQ ID NO: 15 | SEQ ID NO: 16 | SEQ ID NO: 17 |
| NH0267115 | SEQ ID NO: 18 | SEQ ID NO: 19 | SEQ ID NO: 20 | SEQ ID NO: 21 | SEQ ID NO: 22 |
| NI0254582 | SEQ ID NO: 23 | SEQ ID NO: 24 | SEQ ID NO: 25 | SEQ ID NO: 26 | SEQ ID NO: 27 |
| sN10957 | | | | | SEQ ID NO: 28 |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A plant of a cultivated variety of *Brassica oleracea* comprising an introgression that confers resistance to a plurality of *Xanthomonas campestris* pv. *campestris* pathovars relative to a plant lacking said introgression, wherein said resistance is co-dominant and additive, wherein said introgression comprises a chromosomal segment that confers said resistance, wherein the chromosomal segment comprises marker NH0265597 (SEQ ID NO:11), marker NH0265157 (SEQ ID NO:5) and marker NH0266951 (SEQ ID NO:12), and wherein a sample of seed comprising said chromosomal segment was deposited under ATCC Accession Number PTA-123409.

2. The plant of claim 1 defined as a broccoli or cauliflower plant.

3. The plant of claim 1, wherein said introgression lacks an allele genetically linked thereto conferring retarded plant growth in a plant that comprises said allele.

4. The plant of claim 1, wherein said plant is a broccoli, cauliflower, sprouting broccoli, Brussels sprouts, white cabbage, red cabbage, savoy cabbage, curly kale cabbage, turnip cabbage or Portuguese cabbage plant.

5. The plant of claim 1, wherein said plant is not a white cabbage plant.

6. The plant of claim 1, wherein the plant is homozygous for said introgression.

7. A seed that produces the plant of claim 1.

8. A plant part of the plant of claim 1.

9. The plant part of claim 8, wherein the plant part is a cell, a seed, a root, a stem, a leaf, a head, a flower, or pollen.

10. A method for producing a cultivated variety of a *Brassica oleracea* plant with improved resistance to *Xanthomonas campestris* pv. *campestris*, comprising introgressing into said plant variety a chromosomal segment that confers resistance to a plurality of *Xanthomonas campestris* pv. *campestris* pathovars relative to a plant lacking said introgression, and wherein said resistance is co-dominant and additive, wherein the chromosomal segment comprises marker NH0265597 (SEQ ID NO:11), marker NH0265157 (SEQ ID NO:5) and marker NH0266951 (SEQ ID NO:12), and wherein a sample of seed comprising said chromosomal segment was deposited under ATCC Accession Number PTA-123409.

11. The method of claim 10, wherein said introgressing comprises:

a) crossing a plant comprising said chromosomal segment with itself or with a second *Brassica oleracea* plant of a different genotype to produce one or more progeny plants; and b) selecting a progeny plant comprising said chromosomal segment.

12. The method of claim 11, wherein selecting a progeny plant comprises detecting at least one allele comprising marker NH0265597 (SEQ ID NO:11).

13. The method of claim 10, wherein said plant variety is a broccoli, cauliflower, sprouting broccoli, Brussels sprouts, white cabbage, red cabbage, savoy cabbage, curly kale cabbage, turnip cabbage or Portuguese cabbage plant variety.

14. The method of claim 11, wherein the progeny plant is an F2-F6 progeny plant.

15. The method of claim 11, wherein said method further comprises backcrossing.

16. The method of claim 15, wherein said backcrossing comprises from 2-7 generations of backcrosses.

17. A *Brassica oleracea* plant produced by the method of claim 10, wherein said plant comprises said chromosomal segment.

18. A method of producing food or feed comprising obtaining a plant according to claim 1, or a part thereof, and producing said food or feed from said plant or part thereof.

19. A method of producing food or feed comprising obtaining a plant according to claim 17, or a part thereof, and producing said food or feed from said plant or part thereof.

20. The method of claim 10, wherein said introgression lacks an allele genetically linked thereto conferring retarded plant growth in a plant that comprises said allele.

* * * * *